United States Patent [19]

Westermann et al.

[11] Patent Number: 4,601,746

[45] Date of Patent: Jul. 22, 1986

[54] SUBSTITUTED SULFONYLUREA, PROCESSES FOR THE PRODUCTION OF THESE COMPOUNDS, AS WELL AS COMPOSITIONS CONTAINING THE SAME AND HAVING HERBICIDAL AND PLANT GROWTH REGULATING ACTIVITY

[75] Inventors: Jürgen Westermann; Gerhard Boroschewski; Ulrich Eder; Friedrich Arndt; Hansjörg Krähmer; Clemens Kötter, all of Berlin, Fed. Rep. of Germany

[73] Assignee: Schering Aktiengesellschaft, Berlin and Bergkamen, Fed. Rep. of Germany

[21] Appl. No.: 623,134

[22] Filed: Jun. 18, 1984

[30] Foreign Application Priority Data

Jun. 16, 1983 [DE] Fed. Rep. of Germany ....... 3322280

[51] Int. Cl.$^4$ .................... C07D 239/46; A01N 47/36
[52] U.S. Cl. ........................................ 71/92; 544/113; 544/122; 544/208; 544/211; 544/295; 544/321; 544/323; 544/332
[58] Field of Search ................... 71/92; 544/320, 321, 544/331, 332, 323, 113, 122

[56] References Cited

U.S. PATENT DOCUMENTS 4,435,206 3/1984 Levitt ................................... 71/92

Primary Examiner—Robert Gerstl
Attorney, Agent, or Firm—Michael J. Striker

[57] ABSTRACT

New substituted sulfonyl urea are disclosed of the general formula

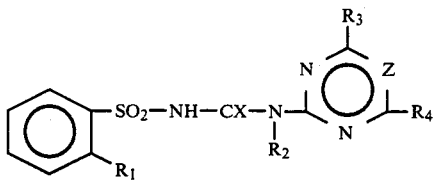

in which
$R_1$ is chlorine, $-COOR_5$, $-S(O)_n-R_6$ or

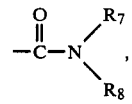

$R_2$ is

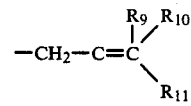

or $-CH_2-C\equiv C-R_{11}$, $R_3$ is hydrogen, $C_1-C_4$-alkyl, $C_1-C_4$-alkylthio, halogen, halogen-$C_1-C_4$-alkyl, halogen-$C_1-C_4$-alkoxy, Di-$C_1-C_3$-alkyl-amino, $C_1-C_3$-alkyl-amino or $C_1-C_3$-alkoxy-$C_1-C_3$-alkoxy, $R_4$ is hydrogen $C_1-C_4$-alkyl, $C_1-C_4$-alkoxy, $C_1-C_4$-alkylthio, halogen, halogen-$C_1-C_4$-alkyl, halogen-$C_1-C_4$-alkoxy, Di-$C_1-C_3$-alkyl-amino, $C_1-C_3$-alkyl-amino, or $C_1-C_3$-alkoxy-$C_1-C_3$-alkoxy, $Z$ is $-CH=$ or $-N=$, $R_5$ is $C_1-C_8$-alkyl, $C_3-C_8$-cycloalkyl, $C_1-C_3$-alkoxy-$C_1-C_3$-alkyl, phenyl, substituted phenyl, benzene or substituted benzene, $R_6$ is $C_1-C_6$-alkyl or phenyl, $R_7$ is $C_1-C_4$-alkyl, $R_8$ is $C_1-C_4$-alkyl, $R_7$ and $R_8$ are independently $C_3-C_8$-cycloalkyl, morpholinyl, pyrrolidinyl, piperidyl or piperazinyl, $R_9$ is hydrogen, chlorine, fluorine, or $C_1-C_3$-alkyl, $R_{10}$ is hydrogen, chlorine, fluorine, trifluoromethyl or $C_1-C_3$-alkyl, $R_{11}$ is hydrogen, chlorine, fluorine, cyano, $C_1-C_4$-alkyl or phenyl, $X$ is oxygen or sulfur, and $n$ is 0, 1 or 2, as well as processes for the preparation of these compounds and compositions having herbicidal and plant growth regulating effectiveness.

17 Claims, No Drawings

SUBSTITUTED SULFONYLUREA, PROCESSES FOR THE PRODUCTION OF THESE COMPOUNDS, AS WELL AS COMPOSITIONS CONTAINING THE SAME AND HAVING HERBICIDAL AND PLANT GROWTH REGULATING ACTIVITY

BACKGROUND OF THE INVENTION

The invention concerns new substituted sulfonyl urea, processes for the production of these compounds as well as compositions containing the same and having herbicidal and plant growth regulating activity.

It is already known to prepare sulfanamide that are useful for the purpose of an herbicidal effectiveness, for example from EP-PS0 001 515. However, these known components of herbicidal compositions have not always shown to be satisfactory in their activity.

It is therefore an object of the present invention to develop new active substances with characteristics that surpass those of the known components.

This object is obtained according to the present invention by new substituted sulfonyl urea of the general formula

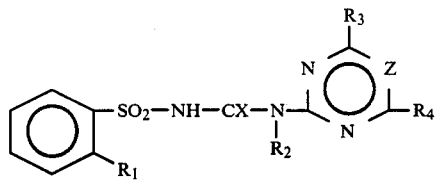

in which
$R_1$ is chlorine, $-COOR_5$, $-S(O)_n-R_6$ or

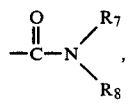

$R_2$ is

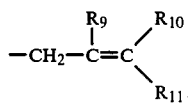

or $-CH_2-C\equiv C-R_{11}$, $R_3$ is hydrogen, $C_1-C_4$-alkyl, $C_1-C_4$-alkoxy, $C_1-C_4$-alkylthio, halogen, halogen-$C_1-C_4$-alkyl, halogen-$C_1-C_4$-alkoxy, Di-$C_1-C_3$-alkyl-amino, $C_1-C_3$-alkyl-amino or $C_1-C_3$-alkoxy-$C_1-C_3$-alkoxy, $R_4$ is hydrogen, $C_1-C_4$-alkyl, $C_1-C_4$-alkoxy, $C_1 14C_4$-alkylthio, halogen, halogen-$C_1-C_4$-alkyl, halogen-$C_1-C_4$-alkoxy, Di-$C_1-C_3$-alkyl-amino, $C_1-C_3$-alkyl-amino or $C_1-C_3$-alkoxy-$C_1-C_3$-alkoxy, Z is $-CH=$ or $-N=$, $R_5$ is $C_1-C_8$-alkyl, $C_3-C_8$-cycloaklyl, $C_1-C_3$-alkoxy-$C_1-C_3$-alkyl, Phenyl, substituted phenyl, benzyl or substituted benzyl, $R_6$ is $C_1-C_6$-alkyl or phenyl, $R_7$ is $C_1-C_4$-alkyl $R_8$ is $C_1-C_4$-alkyl, $R_7$ and $R_8$ are independently $C_3-C_8$-cycloalkyl, morpholinyl, pyrrolidinyl, piperidyl or piperazinyl, $R_9$ is hydrogen, chlorine, flourine or $C_1-C_3$-alkyl, $R_{10}$ is hydrogen, chlorine, flourine, trifluoromethyl or $C_1-CC_3$-alkyl, $R_{11}$ is hydrogen, chlorine, flourine, cyano, $C_1-C_4$-alkyl or phenyl, X is oxygen or sulfur, and n is 0, 1 or 2.

SUMMARY OF THE INVENTION

The substituted sulfonyl urea according to the present invention display an excellent herbicidal activity against difficultly controllable double-nucleated leaf and grass-like annual and perennial weeds.

For example, the following are controlled according to the present invention;

Stellaria, Abutilon, Matricaria, Viola, Centaurea, Amaranthus, Fagopyrum, Helianthus, Brassica, Sesbania, Euphorbia, Daura, Avena fatua, Alopecurus myosuroides, mentha arvenis, Cirsium arvense, Convolvulus arvensis, Sorghum halepense, Cyperus esculentus, Poa annua, Bromus tectorum and Agropyron repens.

Employment of the compounds according to the present invention can be done by pre-seeding, pregermination or post-germination techniques.

The pregermination treatment of weeds takes place on earth that is not overgrown, so that the germinating plants develop up until the germ leaf stage, after which however, occurs a complete stoppage of growth followed by death of the plants after three to five weeks.

The compounds according to the present invention when employed in a post-germination technique, a stoppage of growth takes place quickly after the treatment. In this case the weeds remain at that stage of growth or die completely after a longer period.

The active substances according to the present invention possess an herbicidal activity in advantageous manner even at very low application amounts. Preferably the application amounts lie between 0.010 and 5.0 kg active substance per hectare.

It is also within the scope of the present invention that the active substances are useful in the described manner but for total weed control. Surprisingly, significant main cultures such as for example, corn, barley, wheat, rice, cotton and soybeans, behave resistant, so that the compounds according to the present invention can be employed to great advantage in the selective control of monocotyl and dicotyl, annual and perennial weeds, a result which is only poorly or even not all reached according to today's state of the art.

The compounds according to the present invention moreover, are suitable for influencing the vegetative and generative growth of legumes, such as for example soybeans, and can also even be employed with Graminae. They can thus be employed, based for example upon a retarding effect, for an increase in the sugar content of sugar cane.

By reason of these characteristics the compounds according to the present invention are classified in the category of plant growth regulators, which distinguish through the following use possibilities:

restraint of the vegetative growth of woody and weed plants, for example at road borders, railroad plants, among others, in order to prevent too voluptuous a growth;

growth restraint with grain, in order to prevent depositing or breaking off;

with cotton, in order to increase the yield.

Influencing the branching of vegetative and generative organs with ornamental and cultured plants in order to hasten the onset of blooming or with tobacco and tomato, for the purpose of restraining side-shoots.

Improvement of the food quality, for example an increase in sugar content with sugar cane, sugar beets or fruit;

and a more uniform ripening of the harvest goods, which leads to higher yields.

Increasing the resistance against climatic influence such as cold and dryness.

Influencing the latex flow of rubber plants.

Formation of parthenocarpic fruit, pollen sterility and sexual influence are likewise possibilities of use.

Control of the germination of seeds or the driving out of buds.

Defoliation or influencing the fruit fall in order to facilitate harvesting.

The substances according to the present invention provide these effects not only with a pregermination treatment but also with a post-germination treatment.

The application amounts for the plant growth regulating activities run generally, and depending upon the purpose of use, between 0.005 and 5.0 kg. active substance per hectare. If necessary, however, even higher application amounts can be employed.

The time of use is dependent upon the purpose of use and climatic conditions. Of the compounds according to the present invention, those which distinguish particularly through an outstanding herbicidal and plant growth regulation activity when contrasted to the components known from the state of the art, include the following:

1-allyl-1-(4,6-dimethyl-2-pyrimidinyl)-3-(2-methoxycarbonyl-phenylsulfonyl)-urea, 1-(4,6-dimethyl-2-pyrimidinyl)-2-(2-methoxycarbonyl-phenylsulfonyl)-1-propargyl-urea, 1-allyl-1-(4,6-dimethyl-2-pyrimidinyl-3-(2-ethoxycarbonyl-phenylsulfonyl)-urea, 1-(4,6-dimethyl-2-pyrimidinyl)-3-(2-ethoxycarbonyl-phenylsulfonyl)-1-propargyl-urea, 1-allyl-1-(4,6-dimethoxy-1,3,5-triazin-2-yl)-3-(2-ethoxycarbonyl-phenylsulfonyl)-urea, 1-allyl-1-(4-methoxy-6-methyl-1,3,5-triazin-2-yl)-3-(2-methoxycarbonyl-phenylsulfonyl)-urea, 1-allyl-1-(4-methoxy-6-methyl-1,3,5-triazin-2-yl)-3-(2-ethoxycarbonyl-phenylsulfonyl)-urea.

The compounds according to the present invention can be used either alone, in mixture with one another or with other active substances. If necessary, other plant protection or pest control agents can be added, indeed, according to the desired purpose.

Insofar as a broadening of the activity spectrum is considered, other biocides can be added. For example, suitable as herbicidally effective mixture partners are those active substances that are listed "Lists of common names and abbreviations employed for currently used herbicides and plant growth regulators in weed abstracts". Moreover, even non-phytotoxic agents can be employed which, with herbicide and/or growth regulators, can provide a synergestic increase in activity, such as among others wetting agents, emulsifiers, solvents and oil additives.

Additionally useful as mixture partners are various phospholipids, for example those from the groups phosphatidylcholine, the hydrated phosphatidylcholines, phosphatidylethanolamine, the N-acyl-phosphatidylethanolamines, phosphatidylinosite, phosphatidylserine, lysolecithin and phosphatidylglycerol.

Expediently the characterized active substances or their mixtures are employed in the form of preparations such as powders, spray agents, granulates, solutions, emulsions or suspensions, with the addition of liquid and/or solid carrier substances or diluting agents and, if necessary, wetting, emulsifying, adhering and/or dispersing adjuvants.

Simple liquid carrier substances include by way of example water, aliphatic and aromatic hydrocarbons, such as benzene, toluene, xylene, cyclohexanone, isophoron, dimethylsulfoxide, dimethylformamide, moreover mineral oil fractions and plant oils.

Suitable solid carrier substances include mineral earths, for example, tonsil, silica gel, talcum, kaolin, attapulgite, limestone, silicic acid and plant products, for example, meal.

Surface-active substances worthy of mention include the following, calciumligninsulfonate, polyoxyethylenalkylphenylether, napthalinsulfonic acids and their salts, phenolsulfonic acids and their salts, formaldehyde condensate, fatty alcohol sulfate, as well as substituted benzene sulfuric acids and their salts.

In the event that the active substances should find use for a pickling of seeds, then dyes can also be admixed in order to provide the pickled seeds with a clearly visible coloration.

The portion of the active substance or substances within the different preparations can vary within broad limits. For example, the compositions may contain about ten to ninety percent of active substance, about ninety to ten percent by weight liquid or solid carrier material, as well as if necessary up to twenty percent by weight surface-active substance, upon corresponding reduction in the amount of carrier material.

The application of the active substance can follow in customary manner, for example, with water as carrier in sprayable amounts from about 100 up to 1000 l/ha. An employment of the substances is also possible according to the low-volume or ultra-low-volume techniques, as well as is their application in the form of so-called microgranulates.

The following components are set forth by way of example to illustrate production of the preparations according to the present invention:

A. Spray Powder (a) 40% by weight active substance
  25% by weight clay minerals
  20% by weight silicic acid
  10% by weight cell pitch
  5% by weight surface-active substance based upon a mixture of the calcium salt of lignin sulfonic acid with alkylphenolpolyglycolethers (b) 25% by weight active substance
  60% by weight kaolin
  10% by weight silicic acid
  5% by weight surface-active substance based upon the sodium salt of N-methyl-N-oleyl-taurine and the calcium salt of ligninsulfonic acid (c) 10% by weight active substance
  60% by weight clay minerals
  15% by weight silicic acid
  10% by weight cell pitch
  5% weight surface-active substance based upon the sodium salt of N-methyl-N-oleyl-taurine and the calcium salt of ligninsulfonic acid

B. Paste

45% by weight active substance
5% by weight sodium aluminum silicate
15% by weight catylpolyglycolether with 8 mol ethyleneoxide
2% by weight spindle oil
10% by weight polyethyleneglycol
23 parts water

C. Emulsion concentrate

25% by weight active substance
15% by weight cyclohexanone
55% by weight xylene
5% by weight mixture of nonylphenylpolyoxyethylene or calciumdodecylbenzene sulfonate The compounds according to the present invention can be prepared for example, by reacting compounds of the general formula

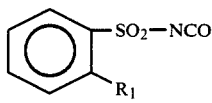

II with compounds of the general formula

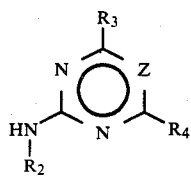

III in the presence of an inert solvent, wherein $R_1$, $R_2$, $R_3$, $R_4$ and Z have the above given meaning.

The production of the compounds according to the present invention of general formula I follows by means of the action of a phenylsulfonylisocyanate of the general formula II with an amine of the general formula III in an inert solvent, such as methylenechloride, acetonitrile, benzene, toluene, 1,2-dichloroethane, tetrahydrofuran, dimethyloxyethane or diethylether, at temperatures between 0° C. and the boiling point of the particular solvent, preferably at 20° C. to 60° C.

The isocyanate of the general formula II can also be prepared in good yields from corresponding sulfamides by means of reaction with oxalylchloride.

The sulfamides per se are manufacturable according to known techniques (JOC 27, 1703 [1962]; Khim. Farm. Zh. 1979, 36; CA 90, 203623 m).

The starting compounds of general formula III are known or can be prepared according to known techniques (D. J. Brown "The Pyrimidines", in A. Weissberger, "The Chemistry of Heterocyclic Compounds", Vol. XVI, New York & London: John Wiley & Sons, 1962; E. M. Smolin and L. Rapoport, "S-Triazines and Derivates", in A. Weissberger, ed., "The Chemistry of Heterocyclic Compounds", Vol. XIII, New York & London: John Wiley & Sons, 1959).

Alkenyl- and alkynylamino compounds of general formula III are obtained by means of condensation of chloro heterocycle with an unsaturated amine.

This occurs preferably in an inert polar solvent, such as for example dimethylformamide, nitroethane, tetrahydrofuran or N-methylpyrrolidon or through reaction in the corresponding amine as solvent. The compounds of formula III are stable substances which can be purified by recrystallization or distillation.

The novel features which are considered characteristic for the invention are set forth in particular in the appended claims. The invention itself, but as to its construction and procedure and its operation and use, together with additional objects and advantages thereof, will be best understood from the following description of specific embodiments.

DESCRIPTION OF THE PREFERRED EMBODIMENTS

EXAMPLE I 1-allyl-3-(2-ethoxycarbonylphenylsulfonyl)-1-(4,6-dimethylprimidine-2-yl)-urea.

At room temperature, 3.31 g. (13 mmol) 2-ethoxycarbonylphenylsulfonylisocyanate are added dropwise to 1.95 g (12.00 mmol) 2-allylamino-4,6-dimethylpyrimidine in 40 ml absolute toluene, and stirred for 4 hours. Subsequently the solvent is separated and the residue chromotographed on silica gel with ethyl acetate as flowing agent.

In this manner are obtained 3.5 g. (70% of theoretical) 1-allyl-3-(2-ethoxycarbonylphenylsulfonyl)-1-(4,6-dimethylpyrimidine-2-yl)-urea.

Mp.: 126°–127° C.

In analogous manner the following compounds according to the present invention are prepared:

| Example No. | Name of Compound | Physical constant (MP except as noted) |
|---|---|---|
| 2 | 1-allyl-1-(4,6-dimethylpyrimidine-2-yl)-3-(2-methoxycarbonylphenylsulfonyl)-urea | 122–124° C. |
| 3 | 1-allyl-3-(2-methoxycarbonylphenylsulfonyl)-1-(4-methoxy-6-methylpyrimidine-2-yl)-urea | 91–93° C. |
| 4 | 1-allyl-1-(4,6-dimethoxy-1,3,5-triazin-2-yl)-3-(2-methoxycarbonylphenylsulfonyl)-urea | 128–130° C. |
| 5 | 1-allyl-1-(4-methoxy-6-methylpyrimidine-2-yl)-3-(2-ethoxycarbonylphenylsulfonyl)-urea | 110–112° C. |
| 6 | 1-allyl-3-(2-ethoxycarbonylphenylsulfonyl)-1-(4-methoxy-6-methyl-1,3,5-triazin-2-yl)-urea | 70–81° C. |
| 7 | 1-allyl-1-(4,6-dimethoxy-1,3,5-triazin-2-yl)-3-(2-ethoxy-carbonylphenylsulfonyl)-urea | 109–110° C. |
| 8 | 1-allyl-3-(2-propoxycarbonylphenylsulfonyl-1-pyrimidine-2-yl)-urea | 90° C. |
| 9 | 1-allyl-3-(2-propoxycarbonylphenylsulfonyl)- | 110° C. |

-continued

| Example No. | Name of Compound | Physical constant (MP except as noted) |
|---|---|---|
|  | 1-(4,6-dimethylpyrimidine-2-yl)-urea |  |
| 10 | 1-allyl-1-(4,6-dimethylpyrimidin-2-yl)-3-(2-isopropoxycarbonylphenylsulfonyl)-urea | 154–155° C. |
| 11 | 1-(4,6-dimethylpyrimidine-2-yl)-3-(2-methoxycarbonylphenylsulfonyl)-1-propargylurea | 163° C. |
| 12 | 1-(4,6-dimethylpyrimidine-2-yl)-3-(2-ethoxycarbonylphenylsulfonyl)-1-propargyl-urea | 145–146° C. |
| 13 | 1-allyl-3-(2-chlorophenylsulfonyl)-1-(4,6-dimethylpyrimidine-2-yl)-urea | 127–131° C. |
| 14 | 1-allyl-3-(2-chlorophenylsulfonyl)-1-(4-methoxy-6-methylpyrimidine-2-yl)-urea | 119–123° C. |
| 15 | 1-allyl-3-(2-chlorophenylsulfonyl)-1-(4-methoxy-6-methyl-1,3,5-triazin-2-yl)-urea | 130–135° C. |
| 16 | 1-allyl-3-(2-chlorophenylsulfonyl)-1-(4,6-dimethoxy-1,3,5-triazin-2-yl)-urea | 149–152° C. |
| 17 | 3-(2-chlorophenylsulfonyl)-1-(4,6-dimethyl-pyrimidine-2-yl)-1-propargyl-urea | 158–160° C. |
| 18 | 1-allyl-1-(4-methoxy-6-methylpyrimidine-2-yl)-3-(2-propoxycarbonylphenylsulfonyl)-urea | 84–91° C. |
| 19 | 1-allyl-1-(4,6-dimethoxy-1,3,5-triazin-2-yl)-3-(2-propoxycarbonylphenylsulfonyl)-urea | 118–12° C. |
| 20 | 1-allyl-3-[2-(2-chloroethoxy)-carbonylphenolsulfonyl]-1-(4,6-dimethylpyrimidine-2-yl)-urea | 141–142° C. |
| 21 | 1-allyl-3-[2-(2-chloroethoxycarbonyl)-phenylsulfonyl-]-1-(4,6-dimethoxy-1,3,5-triazin-2-yl)-urea | 153–155° C. |
| 22 | 1-allyl-1-(4,6-dimethylpyrimidine-2-yl)-3-(2-N—morpholinocarbonylphenylsulfonyl)-urea | 153–154° C. |
| 23 | 1-allyl-1-(4,6-dimethylpyrimidine-2-yl)-3-(2-N—pyrolidinylcarbonylphenylsulfonyl)-urea | 163–165° C. |
| 24 | 1-allyl-3-(2-dimethylaminocarbonylphenylsulfonyl)-1-(4-methoxy-6-methylpyrimidine-2-yl)-urea | 157–159° C. |
| 25 | 1-(2-chloroallyl)-1-(4,6-dimethyl-pyrimidine-2-yl)-3-(2-methoxycarbonyl-phenylsulfonyl)-urea | 149–152° C. |
| 26 | 1-allyl-3-(2-ethoxycarbonylphenylsulfonyl)-1-(pyrimidine-2-yl)-urea | 75–77° C. |
| 27 | 1-(2-chloroallyl)-1-(4,6-dimethoxytriazin-2-yl)-3-methoxycarbonylphenylsulfonyl)-urea | 115–120° C. |
| 28 | 1-(1,1-dichloroprop-1-en-3yl-1-(4,6-dimethylpyrimidine-2-yl)-3-(2-ethoxycarbonylphenylsulfonyl)-urea | 138–140° C. |
| 29 | 1-crotyl-1-(4,6-dimethylpyrimidine-2-yl)-1[2-(ethoxycarbonyl)-phenylsulfonyl]-urea | 141–142° C. |
| 30 | 1-crotyl-1-(4,6-dimethylpyridine-2-yl)-1-(2-(methoxycarbonyl)-phenylsulfonyl)-urea | 110–112° |
| 31 | 1-(4,6,dimethylpyrimidine-2-yl)-1-propargyl-3-(2-propoxycarbonylphenylsulfonyl)-urea | 122–125° C. |
| 32 | 1-(4,6-dimethylpyrimidine-2-yl)-1-propargyl-3-(2-isopropoxycarbonylphenylsulfonyl)-urea | 132–133° C. |
| 33 | 3-(2-butoxycarbonylphenylsulfonyl)-1-(4,6-dimethylpyrimidine-2-yl)-1-propargyl-urea | 125–136° C. |
| 34 | 3-(2-chlorophenylsulfonyl)-1-(3,3-dichoro-prop-2-enyl)-1-(4,6-dimethylpyrimidine-2-yl)-urea | 133–135° C. |
| 35 | 1-(1,1-dichloroprop-1-en-3-yl)-1-(4,6-dimethyl-pyrimidine-2-yl)-3-(2-methoxy-carbonylphenylsulfonyl)-urea | 140–142° C. |
| 36 | 1-(2-chloroallyl)-1-(4,6-dimethylpyrimidine-2-yl)-3-(2-ethoxycarbonylphenylsulfonyl)urea | 158–160° C. |
| 37 | 1-allyl-3-(2-n-butoxycarbonylsulfonyl)-1-(4-methoxy-6-methylpyrimidine-2-yl)-urea | 54–55° C. |
| 38 | 1-allyl-3-(2-allyloxycarbonylphenyl-sulfonyl)-1-(4,6-dimethylpyrimidine-2-yl)-urea | 108–110° C. |
| 39 | 1-allyl-3-(2-chlorophenylsulfonyl)-1-(4-chlor-6-methyl-1,3,5-triazin-2-yl)-urea | 169–174° C. |
| 40 | 1-allyl-1-(4-(N,N—dimethylamino)-6-methoxy-1,3,5-triazin-2-yl)-3-(2-methoxycarbonylphenylsulfonyl)-urea | 132.5–138° C. |
| 41 | 1-allyl-3-(2-methoxycarbonylphenyl-sulfonyl)-1-(4-methoxy-6-propinyloxy-1,3,5-triazin-2-yl)-urea | oil |
| 42 | 1-allyl-3-(2-chlorophenylsulfonyl)-1-(4-ethoxy-6-methoxy-1,3,5-triazin-2- | 95–102° C. |

-continued

| Example No. | Name of Compound | Physical constant (MP except as noted) |
|---|---|---|
| | yl)-urea | |
| 43 | 1-allyl-3-(2-chlorophenylsulfonyl)-1-(4-methoxy-1,3,5-triazin-2-yl)-urea | 104–111° C. |
| 44 | 1-(3-chloroallyl)-3-(2-chlorophenylsulfonyl)-1-(4,6-dimethoxy-1,3,5-triazin-2-yl)-urea | 128–137° C. |
| 45 | 3-(2-chlorophenylsulfonyl)2-2(4-chlor-6-methyl-1,3,5-triazin-2-yl)-1-propargylurea | 130–135° C. |
| 46 | 1-allyl-3-(2-chlorophenylsulfonyl)-1-(4-(N,N—dimethylamino)-6-methoxy-1,3,5-triazin-2-yl)-urea | |
| 47 | 3-(2-chlorophenylsulfonyl)-1-(3,3-dichloroprop-2-enyl)-1-4,6-dimetnyl-pyrimidin-2-yl)-urea | 133–135° C. |
| 48 | 1-(3,3-dicholorprop-2-enyl)-1-(4,6-dimethyl-pyrimidine-2-yl)-2-(2-methoxycarbonylphenylsulfonyl)-urea | 140–142° C. |
| 49 | 1-(3,3-dichloroprop-2-enyl)-1-(4,6-dimethylpyrimidin-2-yl)-3-(2-ethoxycarbonylphenylsulfonyl)-urea | 138–140° C. 138–140° C. |
| 50 | 1-(3,3-dimethylallyl)-1-(4,6-dimethyl-pyrimidin-2-yl)-3-(2-ethoxycarbonyl-fulfonyl)-urea | 165–166° C. decomposition |
| 51 | 1-(4,6-dimethylpyrimidin-2-yl)-3-(2-methoxycarbonylphenylsulfonyl)-1-(3-phenylallyl)-urea | 178–179° C. decomposition |
| 52 | 1-(4,6-dimethylpyrimidin-2-yl)-3-(2-ethoxycarbonylphenylsulfonyl)-1-(3-phenylallyl)-urea | 186–188° C. |
| 53 | 1-(4,6-dimethylpyrimidin-2-yl)-1-methylallyl-3-(2-methoxycarbonylphenyl-sulfonyl)-urea | 190–191° C. decomposition |
| 54 | 3-(2-chlorophenylsulfonyl)-1-(2,4-dimethylpyrimidin-2-yl)-1-methallylurea | 191–192° C. decomposition |
| 55 | 1-(4,6-dimethylpyrimidin-2-yl)-3-(2-ethoxycarbonylphenylsulfonyl)-1-methylallylurea | 194–195° C. decomposition |
| 56 | 1-(2 chloroallyl)-3-(2-chlorophenyl-sulfonyl)-1-(4,6-dimethyl-1,3,5-triazin-2-yl)-urea | 202–203° C. decomposition |
| 57 | 1-(3,3-dichloroallyl)-1-(4,6-dimet yl-1,3,5-triazin-2-yl)-3-(2-methoxycarbonyl-phenylsulfonyl)-urea | 180–182° C. decomposition |
| 58 | 1-(3,3-dichloroallyl)-1-(4,6-dimethyl-1,3,5-triazin-2-yl)-3-(1-ethoxycarbonyl-phenylsulfonyl)-urea | 186–188° C. decomposition |
| 59 | 1-(3-chloroallyl)-1-(4,6-dimethoxy-1,3,5-triazin-2-yl)-3-(2-chlorobenzene-sulfonyl)-urea | 126–128° C. |
| 60 | 1-(3-chloroallyl)-1(4,6-dimethylpyrimidin-2-yl)-3-(2-methoxycarbonylbenzenesulfonyl)-urea | 133–137° C. |
| 61 | 1-allyl-1-(4-n,n-dimethylamino-6-methyl-1,3,5-triazin-2-yl)-3-(2-methoxycarbonyl-benzenesulfonyl)-urea | 144–146° C. |
| 62 | 1-(4,ethoxy-6-methyl-1,3,5-triazin-2-yl)-1-allyl-3-(2-methoxycarbonylbenzene sulfonyl)-urea | 103–105° C. |
| 63 | 1-(3-chloroallyl)-1-(4,6-dimethoxy-1,3,5-triazin-2-yl)-3-(2-methoxycarbonylbenzene-sulfonyl)-urea | |
| 64 | 1-allyl-1-1-(4-(N,N—dimethylamino)-6-methoxy-1,3,5-triazin-2-yl)-3-(2-ethoxy-carbonylbenzenesulfonyl)-urea | 161–163° C. |
| 65 | 1-allyl-3-(2-ethoxycarbonylbenzene-sulfonyl)-1-(2-methoxy-6-propinyloxy-1,3,5-triazin-2-yl)-urea | |
| 66 | 1-allyl-3-(2-chlorobenzenesulfonyl)-1-(4,6-dimethoxyethoxy-1,3,5-triazin-2-yl)-urea | |
| 67 | 1-(3-chloroallyl)-1-(4-methoxy-6-methyl-1,3,5-triazin-2-yl)-3-(2-methoxycarbonyl-benzenesulfonyl)-urea | 108–110° C. |
| 68 | 1-(2-chloroallyl)-1-(4,6-dimethyl-1,3,5-triazin-2-yl)-3-(2-methoxycarbonyl-phenylsulfonyl)-urea | 70–74° C. |

-continued

| Example No. | Name of Compound | Physical constant (MP except as noted) |
|---|---|---|
| 69 | 1-(2-chloroallyl)-1-(4,6-dimethyl-1,3,5-triazin-2-yl)-3-(2-ethoxycarbonylphenylsulfonyl)-urea | oil |
| 70 | 3-(2-chlorophenylsulfonyl)-1-(3,3-dichloroallyl)-1-(4,6-dimethyl-1,3,5,triazin-2-yl)-urea | 174–176° C. |
| 71 | 1-(2-chlorobenzenesulfonyl)-3-(4-methoxy-6-methyl-1,3,5-triazin-2-yl)-3-propargyl-urea | 144–147° C. |
| 72 | 1-(2-methoxycarbonylbenzenesulfonyl)-3-(4-methoxy-6-methyl-1,3,5-triazin-2-yl)-3-propargyl-urea | 120–122° C. |
| 73 | 1-(3-chloroallyl)-1-(4,6-dimethoxy-1,3,5-triazin-2-yl)-3-(2-methoxycarbonylbenzenesulfonyl)-urea | resiny oil |

In accordance with the procedure described in Example 1, further compounds according to the present invention can be manufactured and which are characterized by the substitutions set forth in the following table.

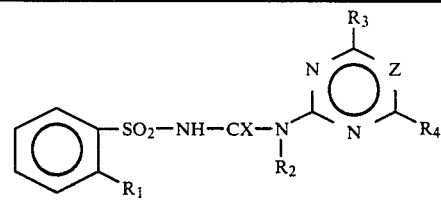

with

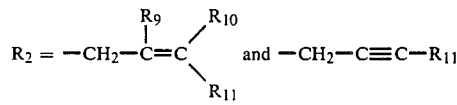

| Example No. | $R_1$ | $R_9$ | $R_{10}$ | $R_{11}$ | $R_3$ | $R_4$ | Z | X |
|---|---|---|---|---|---|---|---|---|
| 46 | $CO_2CH_3$ | H | H | H | $CH_3$ | H | CH | O |
| 47 | $CO_2CH_3$ | H | H | H | $OCH_3$ | $OCH_3$ | CH | O |
| 48 | $CO_2CH_3$ | H | H | H | H | H | CH | O |
| 49 | $CO_2CH_3$ | H | H | H | $CH_3$ | OEt | CH | O |
| 50 | $CO_2CH_3$ | H | H | H | OEt | OEt | CH | O |
| 51 | $CO_2CH_3$ | H | H | H | $CH_3$ | $CH_3$ | N | O |
| 52 | $CO_2CH_3$ | H | H | H | $CH_3$ | $OCH_3$ | N | O |
| 53 | $CO_2CH_3$ | H | H | H | $OCH_3$ | OEt | N | O |
| 54 | $CO_2CH_3$ | H | H | H | CH | $O_3Et$ | N | O |
| 55 | $CO_2CH_3$ | H | H | H | $OCH_3$ | Et | N | O |
| 56 | $CO_2CH_3$ | H | H | H | $CH_3$ | Et | N | O |
| 57 | $CO_2CH_3$ | H | H | H | $NMe_2$ | $CH_3$ | N | O |
| 58 | $CO_2CH_3$ | H | H | H | $NEt_2$ | $CH_3$ | N | O |
| 59 | $CO_2iPr$ | H | H | H | H | $CH_3$ | CH | O |
| 60 | $CO_2iPr$ | H | H | H | $CH_3$ | $OCH_3$ | CH | O |
| 61 | $CO_2iPr$ | H | H | H | $OCH_3$ | $OCH_3$ | N | O |
| 62 | $CO_2iPr$ | H | H | H | H | H | CH | O |
| 63 | $CO_2CH_2CH_2OCH_3$ | H | H | H | H | H | CH | O |
| 64 | $CO_2CH_2CH_2OCH_3$ | H | H | H | $CH_3$ | $CH_3$ | CH | O |
| 65 | $CO_2CH_2CH_2OCH_3$ | H | H | H | $CH_3$ | $OCH_3$ | N | O |
| 66 | $CO_2CH_2CH_2OCH_3$ | H | H | H | $OCH_3$ | $OCH_3$ | N | O |
| 67 | $CO_2CH_3$ | Cl | H | H | $CH_3$ | $OCH_3$ | CH | O |
| 68 | $CO_2Et$ | Cl | H | H | $CH_3$ | $CH_3$ | CH | O |
| 69 | $CO_2Et$ | H | Cl | $CH_3$ | $CH_3$ | $CH_3$ | CH | O |
| 70 | $CO_2CH_3$ | H | $C_6H_5$ | H | $CH_3$ | $CH_3$ | CH | O |
| 71 | $CO_2Et$ | H | $C_6H_5$ | H | $CH_3$ | $CH_3$ | CH | O |
| 72 | $CO_2Pr$ | H | $C_6H_5$ | H | $CH_3$ | $CH_3$ | CH | O |
| 73 | $CO_2CH_3$ | H | H | CN | $CH_3$ | $CH_3$ | CH | O |
| 74 | $CO_2Et$ | H | H | CN | $CH_3$ | $CH_3$ | CH | O |
| 75 | $CO_2CH_3$ | H | $CH_3$ | $CH_3$ | $CH_3$ | $CH_3$ | CH | O |
| 76 | $CO_2Et$ | H | $CH_3$ | $CH_3$ | $CH_3$ | $CH_3$ | CH | O |
| 77 | $CO_2Pr$ | H | $CH_3$ | $CH_3$ | $CH_3$ | $CH_3$ | CH | O |
| 78 | $CO_2Et$ | — | — | H | $OCH_3$ | $CH_3$ | CH | O |
| 79 | $CO_2Et$ | — | — | H | $OCH_3$ | $OCH_3$ | N | O |
| 80 | $CONMe_2$ | H | H | H | $CH_3$ | $CH_3$ | CH | O |
| 81 | Cl | — | — | $CH_3$ | $CH_3$ | $CH_3$ | CH | O |

-continued

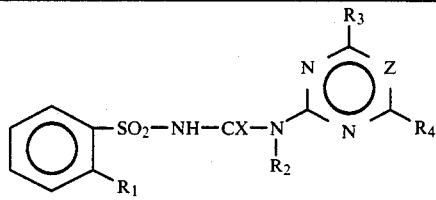

with

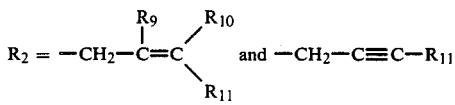

| Example No. | $R_1$ | $R_9$ | $R_{10}$ | $R_{11}$ | $R_3$ | $R_4$ | Z | X |
|---|---|---|---|---|---|---|---|---|
| 82 | $SO_2CH_3$ | H | H | H | $CH_3$ | $CH_3$ | CH | O |
| 83 | $SO_2CH_3$ | H | H | H | $OCH_3$ | $OCH_3$ | N | O |
| 84 | $SO_2CH_3$ | — | — | H | $CH_3$ | $CH_3$ | CH | O |
| 85 | $SO_2C_4H_9$ | H | H | H | $CH_3$ | $CH_3$ | CH | O |
| 86 | $CO_2Et$ | H | H | $CF_3$ | $CH_3$ | $CH_3$ | CH | O |

As mentioned above, the starting compounds for the preparation of those compounds according to the present invention are known per se or can be prepared according to known techniques. Accordingly, the following examples serve to illustrate preparation of the starting compounds.

EXAMPLE 76

2-ethoxycarbonylphenylsulfonylisocyanate

At 85° C., 68.76 g (0.3 mol) 2-sulfamylbenzoic acid ethylester are added to 57.9 g (0.45 mol) oxalylchloride and 0.4 g diazadicyclo(2,2,2,)octane in 500 ml absolute toluene. The reaction mixture is heated yet three hours to an interior temperature of 95° C., until no gas development is observed.

The excess oxalylchloride and toluene are extensively distilled off, decanted of solids, whereupon the product is distilled in high vacuum. One obtains in this manner 63.5 g (83% of theoretical) light yellow oil.

MP: 148° C./0.5 torr.

EXAMPLE 77

2-sulfamylbenzoic acid methylester

An HCl stream is led under cooling into a suspension of 143.3 g (0.78 mol) in 600 ml absolute methanol until saturation. Subsequently the solution is refluxed yet two hours until the saccharine has gone completely into solution and the reaction has terminated.

The excess alcohol is evaporated, the residue is withdrawn in ethyl acetate, and then washed with slightly saturated $Na_2$—$Co_3$— solution for separation of non-converted saccharine. After evaporation of the ethyl acetate in a vacuum, 148.1 g (88% of theoretical) are obtained of 2-sulfamylbenzoic acid ethylester, MP: 122°-124° C.

In analogous manner the following 2-sulfamylbenzoic acid ester are prepared:
ethyl-, n-propyl-, iso-propyl-, 2-methoxyethyl-, 2-ethoxyethyl-, allyl-, butyl-, hexyl-, cyclopentyl-, 2-chloroethyl

EXAMPLE 78

2-allylamino-4,6-dimethylpyrimidine 20 g (0.14 mol) 2-chlor-4,6-dimethylpyrimidine are heated under reflux in 60 ml allylamine. After 4 hours the reaction is terminated. The excess allylamine is distilled off. Thereafter the residue is withdrawn in ethyl acetate and then washed with 150 ml saturated bicarbonate solution. After drying across $Na_2SO_4$ the solvent is discharged. In this manner are obtained 22.5 g (99% of theoretical) 2-allylamino-4,6-dimethylpyrimidine.

MP: 68°-70° C.

In analogous manner the following alkenylaminpyrimidine and -triazine are synthesized from corresponding 2-chloroheterocycles:
2-(2-chloroallylamino)-4,6-dimethylpyrimidine
2-crotylamino-4,6-dimethylpyrimidine
2-phenylamino-4,6-dimethylpyrimidine
2-(1,1,2-trichloroprop-1-en-3-ylamino)-4,6-dimethylpyrimidine
2-allylaminopyrimidine
2-allylamino-4-methoxy-6-methylpyrimidine
2-propargylamino-4,6-dimethyl yrimidine
2-propargylamino-4-methoxy-6-methylpyrimidine
2-(but-2-in-4-ylamino)-4,6-dimethylpyrimidine
2-(4,4,4-trifluorocrotylamino)-4,6-dimethylpyrimidine
2-methallylamino-4,6-dimethylpyrimidine
2-(3-phenylallylamino)-4,6-dimethylpyrimidine
2-allylamino-4,6-dimethyl-1,3,5-triazine
2-allylamino-4-methoxy-6-methyl-1,3,5-triazine
2-allylamino-4,6-dimethoxy-1,3,3-triazine
2-allylamino-4,6-diethoxy-1,3,5-triazine
2-allylamino-4,6-dimethoxypyrimidine The following examples serve as an illustration of the various use possibilities of the compounds according to the present invention, and which follow in the form of the above described preparations:

EXAMPLE 79

In a greenhouse the compounds set forth in the table below in an application amount of 3.0 kg active substance/ha suspended in 500 l water/ha are sprayed onto helianthus and chrysanthemum as test plants in both pregermination and post-germination techniques.

Injury to the weeds is classified three weeks after the treatment according to a scheme ranging from 0 to 4 whereby:

0=no activity

1=moderate growth restraint
2=strong growth restraint
3=complete growth restraint
4=extermination
VA=pre-germination
NA=post-germination

| Compounds According to the Invention | Helianthus VA | Helianthus NA | Chrysanthemum VA | Chrysanthemum NA |
|---|---|---|---|---|
| 1-allyl-1-(4,-6-dimethylpyrimidine-2-yl)-3-(2-methoxycarbonylphenyl-sulfonyl)-urea | 4 | 4 | 4 | 4 |
| 1-allyl-3-(2-methoxycarbonylphenyl-sulfonyl)-1-(4-methoxy-t-methylpyrimidine-2-yl)-urea | 4 | 4 | 4 | 4 |
| 1-allyl-1-(4,6-dimethoxy-1,3,5-triazine-2-yl)-3-(2-methoxycarbonyl-phenylsulfonyl)-urea | 4 | 4 | 4 | 4 |
| 1-allyl-1-(4-methoxy-6-methylpyrimidine-2-yl)-3-(2-ethoxycarbonylphenylsulfonyl)-urea | 4 | 4 | 4 | 4 |
| 1-allyl-3-(2-ethoxycarbonylphenyl-sulfonyl)-1-(4-methoxy-6-methyl-1,3,5-triazine-2-yl)-urea | 4 | 4 | 4 | 4 |
| 1-allyl-1-(4,6-dimethoxy-1,3,5-triazine-2-yl)-3-(2-ethoxycarbonylphenylsulfonyl)-urea | 4 | 4 | 4 | 4 |
| 1-allyl-3-(2-propoxycarbonylphenyl-sulfonyl)-1-(pyrimidine-2-yl)-urea | 4 | 4 | 4 | 4 |
| 1-allyl-3-(2-propoxycarbonylphenyl-sulfonyl)-1-(4,6-d methylpyrimidine-2-yl)-urea | 4 | 4 | 4 | 4 |
| 1-allyl-1-(4,6-dimethylpyrimidine-2-yl)-3-(2-methoxycarbonylphenylsulfonyl)-1-propargylurea | 4 | 4 | 4 | 4 |
| 1-(4,6-dimethylpyrimidine-2-yl)-3-(2-ethoxycarbonylphenylsulfonyl)-1-propargylurea | 4 | 4 | 4 | 4 |
| 1-allyl-3-(2-chlorophenylsulfonyl)-1-(4,6-dimethylpyrimidine-2-yl)-urea | 4 | 4 | 4 | 4 |
| 1-allyl-3-(2-chlorophenylsulfonyl)-1-(4-methoxy-6-methyl-pyrimidine-2-yl)-urea | 4 | 4 | 4 | 4 |
| 1-allyl-3-(2-chlorophenylsulfonyl)-1-(4,6-dimethoxy-1,3,5-triazine-2-yl)-urea | 4 | 4 | 4 | 4 |
| 3-(2-chlorophenylsulfonyl)-1-(4,6-dimethylpyrimidine-2-yl)-1-propargyl-urea | 4 | 4 | 4 | 4 |
| 1-allyl-3-(2-ethoxycarbonylphenyl-sulfonyl)-1-(4-methoxy-6-methyl-1,3,5-triazine-2-yl)-urea | 4 | 4 | 4 | 4 |
| 1-allyl-1-(4,6-dimethylpyrimidine-2-yl)-3-(2-isopropoxycarbonylphenylsulfonyl)urea | 4 | 4 | 4 | 4 |
| 1-allyl-3-(2-chlorophenylsulfonyl)-1-(4-methoxy-6-methyl-1,3,5-triazine-2-yl)-urea | 4 | 4 | 4 | 4 |
| 1-allyl-1-(4-methoxy-6-methylpyrimidine-2-yl)-3-(propoxycarbonylphenylsulfonyl)-urea | 4 | 4 | 4 | 4 |
| 1-allyl-1-(4,6-dimethoxy-1,3,5-triazine-2-yl)-3-(2-propoxycarbonylphenylsulfonyl)-urea | 4 | 4 | 4 | 4 |
| 1-allyl-1-(4,6-dimethylpyrimidine-2-yl)-3-(2-N—pyrolidinylcarbonylphenylsulfonyl)-urea | 4 | 4 | 4 | 4 |
| 1-allyl-3-(2-dimethylaminocarbonylphenyl-sulfonyl)-1-(4-methoxy-6-methylpyrimidine-2-yl)-urea | 4 | 4 | 4 | 4 |
| 1-allyl-3-[2-(2-chloroethoxy)-carbonyl-phenylsulfonyl]-1-(4,6-dimethylpyrimidine-2-yl)-urea | 4 | 4 | 4 | 4 |
| 1-allyl-3-[2-(2-chloroethoxycarbonylphenyl-sulfonyl-]-1-(4,6-dimethoxy-1,3,5-triazine-2-yl)-urea | 4 | 4 | 4 | 4 |
| 1-2-chloroallyl)-1-(4,6-dimethylpyridine-2-yl)-3-(2-methoxycarbonylphenylsulfonyl)-urea | 4 | 4 | 4 | 4 |
| 1-allyl-3-(2-ethoxycarbonylphenylsulfonyl)--1-(pyrimidine-2-yl)-urea | 4 | 4 | 4 | 4 |
| 1-(2-chloroallyl)-1-(4,6-dimethoxy-triazine-2-yl)-3-(methoxycarbonyl-phenylsulfonyl)-urea | 4 | 4 | 4 | 4 |
| 1(1,1-dichloroprop-1-en-3yl)-1-(4,6-dimethylpyrimidine-2-yl)-3-(2-ethoxy-carbonylphenylsulfonyl)-urea | 4 | 4 | 4 | 4 |
| 1-crotyl-1-(4,6-dimethylpyrimidine-2-yl)-1-(2-(ethoxycarbonyl)phenyl-sulfonyl)-urea | 4 | 4 | 4 | 4 |
| 1-crotyl-1-(4,6-dimethylpyrimidine-2-yl)-1-(2-(methoxycarbonyl)phenyl-sulfonyl)-urea | 4 | 4 | 4 | 4 |
| 1-(4,6-dimethylpyrimidine-2-yl)-1-propargyl-3-(2-propoxycarbonylphenyl-sulfonyl)-urea | 4 | 4 | 4 | 4 |
| 1-(4,6-dimethylpyrimidine-2-yl)-1-propargyl-3-(2-isopropoxycarbonyl-phenylsulfonyl)-urea | 4 | 4 | 4 | 4 |
| 3-(2-chlorophenylsulfonyl)-1-(3,3-dichloroprop-2-enyl)-1-(4,6-dimethyl-pyrmidine-2-yl)-urea | 4 | 4 | 4 | 4 |
| 1-(1,1-dichloroprop-1-en-3-yl)-1-(4,6-dimethylpyrimidine-2-yl)-3-(2-methoxycarbonylphenylsulfonyl)-urea | 4 | 4 | 4 | 4 |
| 1-(2-chlorallyl)-1-(4,6-dimethyl-pyrimidine-2-yl)-3-(2-ethoxycarbonyl-phenylsulfonyl)-urea | 4 | 4 | 4 | 4 |
| 1-allyl-3-(2-allyloxycarbonylphenyl-sulfonyl)-1-(4,6-dimethylpyrimidine-2-yl)-urea | 4 | 4 | 4 | 4 |
| 1-allyl-3-(2-chlorophenylsulfonyl)-1-(4-chlor-6-methyl-1,3,5-triazine-2-yl)-urea | 4 | 4 | 4 | 4 |
| 1-allyl-1-(4-(N,N—dimethylamino)-6-methoxy-1,3,5-triazine-2-yl)-3-(2-methoxycarbonylphenylsulfonyl)-urea | 4 | 4 | 4 | 4 |
| 1-allyl-3-(2-methoxycarbonylphenyl-sulfonyl)-1-(4-methoxy-6-propinyloxy-1,3,5-triazine-2-yl)-urea | 4 | 4 | 4 | 4 |
| 1-allyl-3-(2-chlorophenylsulfonyl)-1-(4-ethoxy-6-methoxy-1,3,5-triazine-2-yl)-urea | 4 | 4 | 4 | 4 |
| 1-allyl-3-(2-chlorophenylsulfonyl)-1-(4-methoxy-1,3,5-triazine-2-yl)-urea | 4 | 4 | 4 | 4 |
| 1-(3-chloroallyl)-3-(2-chlorphenyl-sulfonyl)-1-(4,6-dimethoxy-1,3,5-triazine-2-yl)-urea | 4 | 4 | 4 | 4 |
| 3-(2-chlorophenylsulfonyl)-2-(4-chlor-6-methyl-1,3,5-triazine-2-yl)-1-propargyl-urea | 4 | 4 | 4 | 4 |
| 1-allyl-3-(2-chlorophenylsulfonyl)-1-(4-(N,N—dimetnylamino)-6-methoxy-1,3,5-triazine-2-yl)-urea | 4 | 4 | 4 | 4 |
| 1-(3,3-dimethylallyl)-1-4,6-dimethylpyrimidine-2-yl)-3-(2-ethoxycarbonylphenylsulfonyl)-urea | 4 | 4 | 4 | 4 |
| 1-(4,6-dimethylpyrimidine-2-yl)-3-(2-methoxy-carbonylphenylsulfonyl)-1-(3-phenylallyl)-urea | 4 | 4 | 4 | 4 |
| 1-(4,6-dimet ylpyrimidine-2-yl)-3-(2-ethoxycarbonylphenylsulfonyl)-1-(3-phenylallyl)-urea | 4 | 4 | 4 | 4 |
| 1-(4,6-dimethylpyrimidine-2-yl)-1-methallyl-3-(2-methoxycarbonylphenyl-sulfonyl)-urea | 4 | 4 | 4 | 4 |
| 3-(2-chlorophenylsulfonyl)-1-(2,4-dimethylpyrimidine-2-yl)-1-methallyl-urea | 4 | 4 | 4 | 4 |
| 1-(4,6-dimethylpyrimidine-2-yl)-3-(2-ethoxycarbonylphenylsulfonyl-1-methallyl-urea | 4 | 4 | 4 | 4 |
| 1-(2-chloroallyl)-3-(2-chlorophenyl-sulfonyl)-1-(4,6-dimethyl-1,3,5-triazine-2-yl)-urea | 4 | 4 | 4 | 4 |
| 1-(3,3-dichloroallyl)-1-(4,6-dimethyl-1,3,5-triazine-2-yl)-3-(2-methoxycarbonyl-phenylsulfonyl)-urea | 4 | 4 | 4 | 4 |
| 1-(3,3-dichloroallyl)-1-(4,6-dimethyl- | 4 | 4 | 4 | 4 |

-continued

| Compounds According to the Invention | Helianthus VA | Helianthus NA | Chrysanthemum VA | Chrysanthemum NA |
|---|---|---|---|---|
| 1,3,5-triazine-2-yl)-3-(2-4thoxycarbonyl-phenylsulfonyl)-urea | | | | |
| 1-(3-chloroallyl)-1-(4,6-dimethoxy-1,3-5-triazine-2-yl)-3-(2-chlorbenzenesulfonyl)-urea | 4 | 4 | 4 | 4 |
| 1-(3-chloroallyl)-1-(4,6-dimethyl-pyrimidine-2-yl)-3-(2-methoxycarbonyl-benzenesulfonyl)-urea | 4 | 4 | 4 | 4 |
| 1-allyl-1-(4-N,N—dimethylamino-6-methyl-1,3,5-triazine-2-yl)-3-(2-methoxycarbonyl-benzenesulfonyl)-urea | 4 | 4 | 4 | 4 |
| 1-(4,-ethoxy-6-methyl-1,3,5-triazine- | 4 | 4 | 4 | 4 |
| 2-yl)-1-allyl-3-(2-methoxycarbonyl-benzenesulfonyl)-urea | | | | |
| 1-(2-chloroallyl)-1-(4,6-dimethoxy-1,3,5-triazine-2-yl)-3-(2-methoxy-carbonylbenzenesulfonyl)-urea | 4 | 4 | 4 | 4 |
| 1-(2-chlorobenzenesulfonyl)-3-(4-methoxy-6-methyl-1,3,5-triazine-2-yl)-3-propargyl-urea | 4 | 4 | 4 | 4 |
| 1-(2-methoxycarbonylbenzenesulfonyl)-3-(4-methoxy-6-methyl-1,3,5-triazine-2-yl)-3-propargyl-urea | 4 | 4 | 4 | 4 |
| 1-(3-chloroallyl)-1-(4,6-dimethoxy-1,3,5-triazine-2-yl)-3-(2-methoxy-carbonylbenzenesulfonyl)-urea | 4 | 4 | 4 | 4 |

EXAMPLE 80

Seeds of monocotylidenous and dicotylidenous weeds as well as cultured plants, wheat and soybeans are placed in pots with humus-containing sand earth and covered with earth. The compounds according to the present invention as set forth in the following table are applied prior to germination of the weeds onto the earth surface as a suspension with 500 l water/ha in an application amount of 0.1 kg active substance/ha.

After the treatment the test pots are placed in the greenhouse and the test plants are cultivated under favorable growth conditions. Four weeks after the treatment the plant injuries are classified whereby 0=no activity and 4=destruction of the plants. Untreated controls serve for purposes of comparison. As is evident from the following table, all of the weeds are destroyed without injury to the cultured plants.

| Compounds According to the Invention | Wheat | Soy | Helianthus | Stellaria | Abutilon | Viola | Amaranthus | Sesbania | Datura | Avena fatua | Alopecurus m. | Cyperus esculentus | Sorghum halenpenses | Poa annua | Bromus tectorum |
|---|---|---|---|---|---|---|---|---|---|---|---|---|---|---|---|
| 1-(4,6-dimethyl-pyrimidine-2-yl)-3-(2-ethoxycarbonyl-phenylsulfonyl)-1-propargyl-urea | 0 | 0 | 3 | 3 | 3 | 3 | 3 | 3 | 3 | 2 | 2 | 2 | 2 | 2 | 2 |
| 1-allyl-1-(4-methoxy-6-methylpyrimidine-2-yl)-3-(2-ethoxycarbonyl-phenylsulfonyl urea | 0 | 0 | 4 | 4 | 3 | 4 | 4 | 4 | 4 | 2 | 3 | 2 | 3 | 3 | 3 |
| untreated | 0 | 0 | 0 | 0 | 0 | 0 | 0 | 0 | 0 | 0 | 0 | 0 | 0 | 0 | 0 |

EXAMPLE 81

Seeds of two-nucleated leaf weeds and of wheat and soybeans are sowed in pots and placed in a greenhouse under favorable growth conditions. Three weeks after the sowing the test plants are treated at the 1 to 4 leave stage. For this purpose the compounds are provided as a suspension with 500 l water/ha in the application amounts set forth below. Four weeks after the treatment the plant injuries are classified according to the scheme 0 signifies no activity and 4 signifies destruction of the plants. The results of this test similarly evidenced a high selectivity of the compounds according to the present invention with excellent activity against the weeds.

| Compounds According to the Invention | Application Amts. (AS/ha) | Wheat | Soy | Helianthus | Brassica | Stellaria | Abutilon | Sida | Viola | Amaranthus | Sesbania | Datura | Euphorbia | Avena fatua |
|---|---|---|---|---|---|---|---|---|---|---|---|---|---|---|
| 1-(4,6-dimethylpyrimidine-2-yl)-3-(2ethoxycarbonylphenylsulfonyl)-1-propargyl-urea | 0.1 | — | 0 | 3 | 3 | 3 | 3 | 3 | 3 | 3 | 3 | 3 | 3 | 2 |
| 1-allyl-1-(4-methoxy-6-methylpyrimidine-2-yl)-3-(2-ethoxycarbonylphenylsulfonyl)-urea | 0.1 | — | 0 | 3 | 3 | 3 | 3 | 3 | 3 | 3 | 3 | 3 | 3 | 2 |
| 1-allyl-1-(4,6-dimethoxy-1,3,5-triazine-2-yl)-3-(2-ethoxycarbonylphenylsulfonyl urea | 0.03 | 0 | 0 | 3 | 3 | 3 | 3 | 3 | 3 | 3 | 3 | 3 | 3 | 3 |
| 1-allyl-3-(2-ethoxycarbonylphenylsulfonyl)-1-(4-methoxy-6-methyl-1,3,5-triazine-2-yl)-urea | 0.03 | 0 | 0 | 3 | 3 | 3 | 3 | 3 | 3 | 3 | 3 | 3 | 3 | 3 |
| 1-allyl-1-(4,6-dimethylpyrimidine- | 0.03 | — | 0 | 3 | 3 | 3 | 3 | 3 | 3 | 3 | 3 | 3 | 3 | 3 |

| | Application Amt. | | | | | | | | | | | | |
|---|---|---|---|---|---|---|---|---|---|---|---|---|---|
| 2-yl)-3-(2-methoxy-carbonylphenyl-sulfonyl)-urea | | | | | | | | | | | | | |
| 1-allyl-3-(2-chlor-phenylsulfonyl)-1-(4,6-dimethoxy-1,3,5-triazine-2-yl)-urea | 0.03 | 0 | 0 | 3 | 3 | 3 | 3 | 3 | 3 | 3 | 3 | 3 | 3 | — |
| 1-allyl-3-(2-ethoxycarbonylphenyl-sulfonyl)-1-(4-methoxy-6-methyl)-1,3,5-triazine-2-yl)-urea | 0.03 | 0 | 0 | 3 | 3 | 3 | 3 | 3 | 3 | 3 | 3 | 3 | 3 | — |
| untreated | | 0 | 0 | 0 | 0 | 0 | 0 | 0 | 0 | 0 | 0 | 0 | 0 | |

| Compounds According to the Invention | Application Amts. (AS/ha) | Alopecurus m. | Cyperus esculentus | Sorghum halepense | Poa annua | Bromus tectorum |
|---|---|---|---|---|---|---|
| 1-(4,6-dimethylpyrimidine-2-yl)-3-(2ethoxy-carbonylphenylsulfonyl)-1-propargyl-urea | 0.1 | 2 | 2 | 2 | 2 | 2 |
| 1-allyl-1-(4-methoxy-6-methylpyrimidine-2-yl)-3-(2-ethoxycar-bonylphenylsulfonyl)-urea | 0.1 | 2 | 2 | 2 | 2 | 2 |
| 1-allyl-1-(4,6-dimethoxy-1,3,5-triazine-2-yl)-3-(2-ethoxycarbonylphenyl-sulfonyl urea | 0.03 | 3 | 3 | 3 | 3 | 3 |
| 1-allyl-3-(2-ethoxycar-bonylphenylsulfonyl)-1-(4-methoxy-6-methyl-1,3,5-triazine-2-yl)-urea | 0.03 | 2 | 2 | 3 | 3 | 3 |
| 1-allyl-1-(4,6-dimethylpyrimidine-2-yl)-3-(2-methoxy-carbonylphenyl-sulfonyl)-urea | 0.03 | 3 | 3 | 3 | 3 | 3 |
| 1-allyl-3-(2-chlor-phenylsulfonyl)-1-(4,6-dimethoxy-1,3,5-triazine-2-yl)-urea | 0.03 | — | — | — | — | — |
| 1-allyl-3-(2-ethoxycarbonylphenyl-sulfonyl)-1-(4-methoxy-6-methyl)-1,3,5-triazine-2-yl)-urea | 0.03 | — | — | — | — | — |
| untreated | | 0 | 0 | 0 | 0 | 0 |

EXAMPLE 82

The test substances set forth below are applied dissolved in an acetone-containing lanolin oil to pinto beans. The application is effected after the second internode has attained a length of 2 mm. 10 μg active substance are applied. The evaluation is made four days after the application. The developing second internodes are in part very strongly restrained as to growth.

| Compound According to the Invention | Restraint of Growth in % |
|---|---|
| 1-allyl-1-(4,6-dimethylpyrimidine-2-yl)-3-(2-methoxycarbonylphenylsulfonyl)-urea | 40 |
| 1-allyl-3-(2-chlorophenylsulfonyl)-1-(4,6-dimethoxy-1,3,5-triazine-2-yl)urea | 27 |
| 1-allyl-1-(4,6-dimethoxy-1,3,5-triazine-2-yl)-3-(2-methoxycarbonylphenylsulfonyl)-urea | 54 |
| 1-allyl-3-(2-chlorophenylsulfonyl)-1-(4-methoxy-6-methylpyrimidine-2-yl)-urea | 89 |
| 1-allyl-3-(2-methoxycarbonylphenylsulfonyl)-1-(4-methoxy-6-methylpyrimidine-2-yl)-urea | 43 |
| 1-(4,6-dimethylpyrimidine-2-yl)-3-(2-ethoxycarbonylphenylsulfonyl)-1-propargyl-urea | 42 |
| 1-allyl-1-(4,6-dimethoxy-1,3,5-triazine-2-yl)-3-(2-ethoxycarbonylphenylsulfonyl-urea | 44 |
| 1-allyl-1-(4-methoxy-6-methylpyrmidine-2-yl)-3-(2-ethoxycarbonylphenylsulfonyl)-urea | 63 |
| 1-(4,6-dimethylpyrimidine-2-yl)-3-(2-methoxycarbonylphenylsulfonyl)-1-propargyl-urea | 75 |
| Control | 0 |

It will be understood that each of the elements described above, or two or more together, may also find a useful application in other types of plant growth control different from the types described above.

While the invention has been illustrated and described as embodied in substituted sulfonyl urea, processes for the production of these compounds as well as compositions containing the same and having herbicidal and plant growth regulating activity, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed to be new and desired to be protected by Letters Patent is set forth in the appended claims.

We claim:

1. Sulfonyl urea of the formula

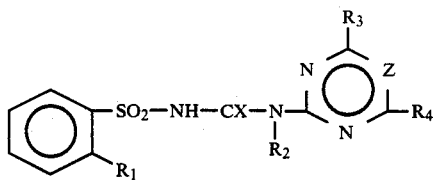

in which $R_1$ is chlorine, $-COOR_5$, $-S(O)_n-R_6$ or

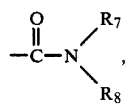

$R_2$ is

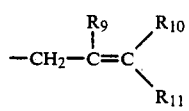

or $-CH_2-C\equiv C-R_{11}$, $R_3$ is hydrogen, $C_1-C_4$-alkyl, $C_1-C_4$- alkylthio, halogen, halogen-$C_1-C_4$-alkyl, halogen-$C_1-C_4$-alkoxy, Di-$C_1-C_3$-alkyl-amino, $C_1-C_3$-alkyl-amino or $C_1-C_3$-alkoxy-$C_1-C_3$-alkoxy, $R_4$ is hydrogen, $C_1-C_4$-alkyl, $C_1-C_4$-alkoxy, $C_1-C_4$-aklylthio, halogen, halogen-$C_1-C_4$-alkyl, halogen-$C_1-C_4$-alkoxy, Di-$C_1-C_3$-alkyl-amino, $C_1-C_3$-alkyl-amino or $C_1-C_3$-alkoxy-$C_1-C_3$-alkoxy, Z is $-CH=$, $R_5$ is $C_1-C_8$-alkyl, $C_3-C_8$-cycloalkyl, $C_1-C_3$-alkoxy-$C_1-C_3$-alkyl, phenyl, or benzyl, $R_6$ is $C_1-C_6$-alkyl or phenyl, $R_7$ is $C_1-C_4$-alkyl, $R_8$ is $C_1-C_4$-alkyl, $R_7$ and $R_8$ are together with the adjacent nitrogen atom, morpholinyl, pyrrolidinyl, piperidyl or piperazinyl, $R_9$ is hydrogen, chlorine, flourine, or $C_1-C_3$-alkyl, $R_{10}$ is hydrogen, chlorine, fluorine, trifluoromethyl or $C_1-C_3$-alkyl, $R_{11}$ is hydrogen, chlorine, fluorine, cyano, $C_1-C_4$-alkyl or phenyl, X is oxygen or sulfur, and n is 0, 1 or 2.

2. The compound according to the claim 1, 1-allyl-1-(4,6-dimethylpyrimidine-2-yl)3-(2-methoxycarbonylphenylsulfonyl)-urea.

3. The compound according to claim 1, 1-allyl-3-(2-methoxycarbonylphenylsulfonyl)-1-(4-methoxy-6-methylpyrimidine-2-yl)-urea.

4. The compound according to claim 1, 1-allyl-1-(4,6-dimethoxy-1,3,5-triazine-2-yl)-3-(2-methoxycarbonylphenylsulfonyl)-urea.

5. The compound according to claim 1, 1-allyl-1-(4-methoxy-6-methylpyrimidine-2-yl)-3-(2-ethoxycarbonylphenylsulfonyl)-urea.

6. The compound according to claim 1, 1-allyl-3-(2-ethoxycarbonylphenylsulfonyl)-1-(4-methoxydimethyl-1,3,5-triazine-2-yl)-urea.

7. The compound according to claim 1, 1-allyl-1-(4,6-dimethoxy-1,3,5-triazine 2-yl)-3-(2-ethoxycarbonylphenylsulfonyl)-urea.

8. The compound according to claim 1, 1-(4,6-dimethylpyrimidine-2-yl)-2-(2-methoxycarbonylphenylsulfonyl)-1-propargyl-urea.

9. The compound according to claim 1, 1-(4,6-dimethylpyrimidine-2-yl)-3-(2-ethoxycarbonylphenylsulfonyl)-1-propargyl-urea.

10. The compound according to claim 1, 1-allyl-3-(2-chlorophenylsulfonyl)-1-(4-methoxy-6-methylpyrimidine-2-yl)-urea.

11. The compound according to claim 1, 1-allyl-3-(2-chlorophenylsulfonyl)-1-(4-methoxy-6-methyl 1,3,5-triazine-2-yl)-urea.

12. The compound according to claim 1, 1-allyl-3-(2-chlorophenylsulfonyl)-1-(4,6-dimethoxy-1,3,5-triazine-2-yl)-urea.

13. Composition with herbicidal and plant growth regulating activity, comprising an effective amount of a compound according to claim 1 in carrier means.

14. The composition according to claim 13, further comprising additives.

15. The composition according to claim 13, wherein concentration of said compound is between 10 and 90 percent by weight.

16. Method for the selective control of weeds, comprising applying onto or within the locus of said weeds an effective amount of the composition according to claim 13.

17. Method for regulating the growth of plants, comprising applying onto or within the locus of said plants a growth regulating effective amount of the composition according to claim 13.

* * * * *